United States Patent
Seesselberg et al.

(10) Patent No.: US 9,259,152 B2
(45) Date of Patent: Feb. 16, 2016

(54) APPARATUS FOR DETERMINING AN AMETROPIA OF AN EYE

(71) Applicants: Carl Zeiss AG, Oberkochen (DE); Carl Zeiss Meditec AG, Jena (DE)

(72) Inventors: Markus Seesselberg, Aalen (DE); Tobias Breuninger, Herbrechtingen (DE); Marco Wilzbach, Stuttgart (DE)

(73) Assignees: CARL ZEISS MEDITEC AG, Jena (DE); CARL ZEISS AG, Oberkochen (DE)

(*) Notice: Subject to any disclaimer, the term of this patent is extended or adjusted under 35 U.S.C. 154(b) by 0 days.

(21) Appl. No.: 14/577,235

(22) Filed: Dec. 19, 2014

(65) Prior Publication Data

US 2015/0173609 A1 Jun. 25, 2015

(30) Foreign Application Priority Data

Dec. 20, 2013 (DE) .................. 10 2013 021 974

(51) Int. Cl.
*A61B 3/00* (2006.01)
*A61B 3/103* (2006.01)
*A61B 3/13* (2006.01)
(Continued)

(52) U.S. Cl.
CPC .............. *A61B 3/103* (2013.01); *A61B 3/0008* (2013.01); *A61B 3/0025* (2013.01); *A61B 3/0083* (2013.01); *A61B 3/1035* (2013.01);
(Continued)

(58) Field of Classification Search
CPC .... A61B 3/0025; A61B 3/113; A61B 3/1015; A61B 3/10; A61B 3/103; A61B 3/1035; A61B 3/1173; A61B 3/13

USPC .................. 351/221, 246, 206, 205; 356/479
See application file for complete search history.

(56) References Cited

U.S. PATENT DOCUMENTS 5,470,329 A * 11/1995 Sumiya .................. A61F 9/008
606/4
6,736,510 B1 5/2004 Van Heugten
(Continued)

FOREIGN PATENT DOCUMENTS

DE 10 2005 005 932 A1 8/2006
DE 10 2005 022 125 A1 11/2006
(Continued)

OTHER PUBLICATIONS

Wesemann, W., "Funktionsprinzipien and Messgenauigkeit moderner Autorefraktometer", DOZ Optometrie, 2004, pp. 38-44 (with English translation thereof).
(Continued)

*Primary Examiner* — Hung Dang
(74) *Attorney, Agent, or Firm* — Patent Portfolio Builders PLLC

(57) ABSTRACT

An apparatus for determining an ametropia of an eye 3 comprises a measurement light source 15 and beam formation optics 17 and an analysis module 35 comprising a detector 39 and analysis optics 37. The analysis optics are configured to focus a parallel light beam, entering through the optical interface 27, along a predetermined line extending transverse to a direction of the analysis beam path. The detector is a spatially resolving detector, wherein an acute angle between a surface normal of the detection area and the predetermined line is less than 80°. A controller 53 is configured to obtain light intensity data detected by the detector and to determine ametropia-data representing the ametropia of the eye based on the light intensity data.

23 Claims, 13 Drawing Sheets

(51) Int. Cl.
*G02B 21/22* (2006.01)
*G02B 21/00* (2006.01)

(52) U.S. Cl.
CPC .................. *A61B 3/13* (2013.01); *A61B 3/132* (2013.01); *G02B 21/22* (2013.01); *G02B 21/0012* (2013.01)

(56) References Cited

U.S. PATENT DOCUMENTS

| | | |
|---|---|---|
| 2008/0030682 A1 | 2/2008 | Teige et al. |
| 2010/0271594 A1 | 10/2010 | Bergner et al. |
| 2012/0069303 A1 | 3/2012 | Seesselberg et al. |
| 2013/0076960 A1 | 3/2013 | Bublitz et al. |
| 2013/0214121 A1 | 8/2013 | Lee et al. |
| 2015/0109580 A1* | 4/2015 | Hauger ................ A61B 3/13 351/206 |

FOREIGN PATENT DOCUMENTS

| | | |
|---|---|---|
| DE | 10 2007 017 599 A1 | 10/2008 |
| DE | 10 2008 047 400 A1 | 4/2010 |
| DE | 10 2010 024 606 A1 | 12/2011 |
| DE | 10 2011 106 288 A1 | 1/2013 |
| DE | 10 2012 012 281 A1 | 12/2013 |

OTHER PUBLICATIONS

Trusit, D., "Automated refraction", Optometry Today OT, 2004, pp. 28-32.
German Decision to Grant, with translation thereof, for corresponding DE application No. 10 2013 021 974.4, dated Dec. 1, 2014.

* cited by examiner

APPARATUS FOR DETERMINING AN AMETROPIA OF AN EYE

CROSS-REFERENCES TO RELATED APPLICATIONS

The present application claims priority of Patent Application No. 10 2013 021 974.4, filed Dec. 20, 2013 in Germany, the entire contents of which, are incorporated by reference herein.

FIELD

The present, invention relates to an apparatus for determining an ametropia of an eye.

BACKGROUND

Apparatuses for determining the ametropia of eyes are suitable for determining the refractive error of an eye of a patient. This determining is the basis for prescriptions of corrective lenses, such as spectacles or contact lenses, for correcting the refractive error of the eye. Data obtained by such an apparatus conventionally comprise an amount of a spherical refractive error and an amount and an orientation of an astigmatic refractive error.

Such conventional apparatuses also referred to as auto refractors may comprise a wave front sensor such as, a Hartmann-Shack-sensor. For measuring the ametropia, a small region on the retina of the eye to be inspected is illuminated by a measurement light, beam. The light of the measurement light, beam reflected at the retina is emitted from the eye and is directed onto an entrance window of the wave front sensor. Subsequently, the ametropia of the eye may be determined based on the measured wave front.

While providing a relatively high measurement accuracy, apparatuses for determining the ametropia of an eye comprising a wave front sensor are expensive devices.

Accordingly, it is an objective of the present invention to propose an apparatus for determining the ametropia of an eye which is realizable simpler and, thus, less expensive and, in particular, does not have a wave front sensor.

SUMMARY

According to embodiments an apparatus for determining an ametropia of an eye comprises a beam generation module comprising a measurement light source and beam formation optics; an analysis module comprising a detector and analysis optics; and a controller; wherein the beam formation optics are configured to form a measurement light beam from light emitted by the measurement light source so that the measurement light beam is emitted from the apparatus at an optical interface; wherein the analysis optics are disposed in an analysis beam path between the optical interface and the detector; wherein the analysis optics are configured to focus a parallel light beam, entering through the optical interface, along a predetermined line extending transverse to a direction of the analysis beam path; wherein the detector is a spatially resolving detector having a detection area; wherein an acute angle between a surface normal of the detection area and the predetermined line is less than 80°; and wherein the controller is configured to obtain light intensity data detected by the detector and to determine ametropia-data representing the ametropia of the eye based on the light intensity data.

For determining the ametropia of an eye, the eye is disposed opposite to the optical interface in a way that the measurement light beam formed by the beam formation optics and emitting from the apparatus through the optical interface enters the eye and illuminates a small region on the retina of the eye. The measurement light reflected and scattered, respectively, in the illuminated region of the retina is formed as a beam by the lens of the eye, the beam is emitted from the eye and enters the optical interface of the apparatus and traverses the analysis beam path of the apparatus. If the eye is an emmetropic eye, i.e., an eye without a refractive error, the beam of measurement light emitted from the eye and entering the analysis optics is a parallel light beam. Said light beam is focused to a line focus by the analysis optics. Such line focus may be generated, for example, by a cylinder lens. This kind of focus is different from a focus generated by a spherical lens from a parallel beam, as the spherical lens generates a focus, the highest light intensities of which are formed in a point and a small circular spot, respectively. The line focus generates highest light intensities along a line and a region extending along a line, wherein the extension of the region is substantially greater along the line than transverse to the line. The line may be a straight line, but also a line curved in space. The focused light beam has an increasing cross section at increasing distance from the focus line in the beam, path before the focus line. Also, the focused light, beam has an increasing beam cross section at increasing distance from the line in the beam path behind the line.

The detector is a spatially resolving detector which allows to determine light intensities depending on a location of incidence of the light on the detector using the detector. For this, the detector may be a one dimensional, spatially resolving detector by, for example, having an array of detection elements and pixels, respectively, extending along a line, or the detector may be a two dimensional, spatially resolving detector by, for example, having a two dimensional, aerially extended array of detection elements. For this, also the one dimensional, spatially resolving detector has a detection area onto which the light to be detected is incident and which contains the detection areas of the individual detection elements disposed along a line.

The spatially resolving detector is disposed in a way that the focus line intersects the detection area of the detector. For this, the detector is orientated in a way an acute angle between a surface normal of the detection area of the detector and the focus line is less than 80°.

According to specific embodiments, this angle may be less than 70°, in particular less than 80° or less than 50°. Further, this angle may be greater than 10°, greater than 20°, greater than 30° or greater than 40°.

Therefore, some sections of the detection area are disposed in the beam path before the focus line and other sections of the detection area are disposed in the beam path behind the focus line. The focused light beam has its smallest cross section and, thus, its highest light intensity per unit area where the focus line intersects the detection area, whereas the focused light beam has, in the other sections where the light beam is incident onto the detection area, a cross section increasing with increasing distance from the focus line and, thus, a decreasing light intensity per unit area. Using the spatially resolving detector detecting the intensity of the incident light in dependence of position, the position, on the detector may be determined where the detected light intensity is at maximum. At this position, the focus line intersects the detection area.

The determining of the position where the focus line intersects the detection area using the maximum detected light intensity is possible using a one dimensional spatially resolving detector. Using a two dimensional spatially resolving detector, it is further possible to obtain the shape of the cross section of the focused light beam projected onto the detection area. This shape is a streak having a minimum width where the focus line intersects the detection area and having a continuously increasing width at increasing distance from this position. This shape of a waist may be analyzed and the position on the detector, where the width of the illuminated streak has a minimum and the detected light intensity has a maximum, may be determined as the position where the focus line intersects the detection area. This position, may be determined, in case of the one dimensional spatially resolving detector by an appropriate analysis of the spatially-dependent detected light intensities and in the case of the two dimensional spatially resolving detector by an appropriate analysis of the spatially-dependent detected light intensities and the shape of the streak illuminated on the detection area, at an accuracy greater than an accuracy corresponding to the distance between neighboring detection elements of the detector (sub-pixel resolution).

If the eye has an ametropia such as a spherical refractive error, then, the beam entering through the optical interface is not a parallel beam but a divergent or convergent beam. Accordingly, a focus line is formed which, in comparison to an emmetropic eye, has a longer or shorter distance from the analysis optics so that the focus line intersects the detection area at positions depending the spherical refractive error of the eye. For example, for a myopic eye, i.e. a short-sighted eye, and the analysis optics being refractive optics or diffractive optics, the focus line is formed at a distance from the analysis optics being less than that for an emmetropic eye. For a hyperopic eye, i.e., a far-sighted eye, the focus line is formed at a distance from the analysis optics being greater than that for an emmetropic eye.

The analysis optics are configured to focus a parallel light beam along a line. Optics having this property are referred, to as anamorphic optics.

According to exemplary embodiments, the analysis optics comprise, for generating the line focus, at least one anamorphic optical element, in particular a cylinder lens, an optical element having the effects of a cylinder lens, or a diffractive optical element.

According to exemplary embodiments, the anamorphic optical element is a lens element having at least one lens surface having, along a line on the lens surface, local radii of curvature continuously increasing along the line.

According to exemplary embodiments, the analysis optics comprise at least one optical element being rotatable relative to the detector about an axis of rotation orientated parallel to the direction of the analysis beam path.

According to exemplary embodiments, the rotatable optical, element is the anamorphic optical element, the cylinder lens, the optical element having the effects of a cylinder lens, or the diffractive optical element.

Due to the rotation of this optical element relative to the detector, the orientation of the line focus is changed in space. If the eye does not have an astigmatic refractive error, the orientation of the line focus changes without changing the distance of the line focus from the analysis optics. However, if the eye has an astigmatic refractive error, not only the orientation of the line focus but also its distance from the analysis optics changes upon rotation of the optical element. By analyzing the light intensities detected by the spatially resolving detector, it is possible to determine this distance in dependence of the rotational position of the optical element relative to the detector and, hence, to determine the amount of the astigmatic refractive error as well as the orientation of the astigmatic refractive error.

According to further embodiments, the analysis optics comprise, beside the anamorphic optical element, the cylinder lens, the optical element having the effects of a cylinder lens, or the diffractive optical element, an additional optical element being rotatable relative to the detector about the axis of rotation. In this case, the anamorphic optical element, the cylinder lens, the optical element having the effects of a cylinder lens, or the diffractive optical element may be fixedly disposed relative to the remaining components of the apparatus and the rotation of the line focus in space may be achieved by the additional optical element being rotatable relative to the detector. According to exemplary embodiments, wherein, the additional optical element is a prism, such as a Schmidt-Pechan-prism, an Abbe-König-prism or a Dove-prism.

According to exemplary embodiments, the analysis optics comprise a drive controlled by the controller and being configured to rotate the rotatable optical element about the axis of rotation. For this, the controller may be configured to rotate the rotatable optical element to a plurality of rotational positions about the axis of rotation, to obtain light intensity data for each of the plurality of rotational positions, and to determine the ametropia-data based on the plurality of obtained light intensity data. In particular, the plurality of obtained light intensity data comprises light intensity data obtained at different rotational positions of the plurality of rotational positions.

According to exemplary embodiments herein, the controller is configured to determine an amount of a spherical refractive error of the eye based on an extremum value of the detected distance of the line focus from the analysis optics. According to further exemplary embodiments herein, the controller is configured to determine the amount of the astigmatic refractive error of the eye based on a difference between a maximum value and a minimum value of the distance of the line focus from the analysis optics.

According to further exemplary embodiments herein, the controller is configured to determine the orientation of an astigmatic refractive error of the eye based on a phase of a dependency of the values representing the position of the beam waist, on the rotational position.

According to further exemplary embodiments, the apparatus comprises a beam splitter which is disposed in a beam path between the beam generation module and the optical interface and in a beam path between the optical interface and the analysis module. Thereby, it is possible to geometrically superimpose the measurement light beam formed, by the beam formation optics with the analysis beam path so that both beam paths traverse the optical interface so that, the measurement light formed by the beam formation optics enters the eye and the light emitted from the eye gets to the analysis optics.

According to exemplary embodiments, a magnified-imaging telescope, i.e. a telescope imaging in a magnifying way, is disposed in a beam path between the optical interface and the detector, thereby increasing the measurement range with respect to a maximum measurable spherical and astigmatic refractive error for a given extension of the detection area and diameter of the measurement light beam. The telescope may be, for example, a Kepler-telescope, a Galilei-telescope or a mirror-telescope. Conventionally, a telescope has a refractive power of 0. However, an optical system may also be disposed in the beam path before the detector, the system having a refractive power different from 0. In particular, a magnifying optical system may also be disposed in the beam path before the detector, the system having a refractive power different from 0.

According to exemplary embodiments, the apparatus comprises at least one rest element positioned relative to the optical interface so that an eye of a user and a patient, respectively, is positioned opposite to the optical interface if a predetermined portion of a head, such as a chin or a forehead, of the user and patient, respectively, is pressed against the rest element.

According to exemplary embodiments, the apparatus comprises a housing encasing the beam generation module and the analysis module and, in particular, protects the analysis module from stray light and extraneous light wherein the housing has an opening, in particular, defining the optical interface, i.e., an emitting cross section of the measurement light beam from the housing and an entering cross section of the beam of measurement light emitted from the eye and getting to the analysis optics. Furthermore, protection from extraneous light may also or in addition be achieved by disposing an optical filter in the beam path of the analysis module before the detector, the optical filter being configured to pass only light of wavelengths also contained in the light emitted by the measurement light, source.

According to further exemplary embodiments, the apparatus is integrated in a microscope, in particular a surgery microscope, having an imaging beam path traversing the optical interface. The microscope may be a stereo microscope.

BRIEF DESCRIPTION OF THE DRAWINGS

The forgoing as well as other advantageous features of the disclosure will be more apparent, from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

Figure 1:
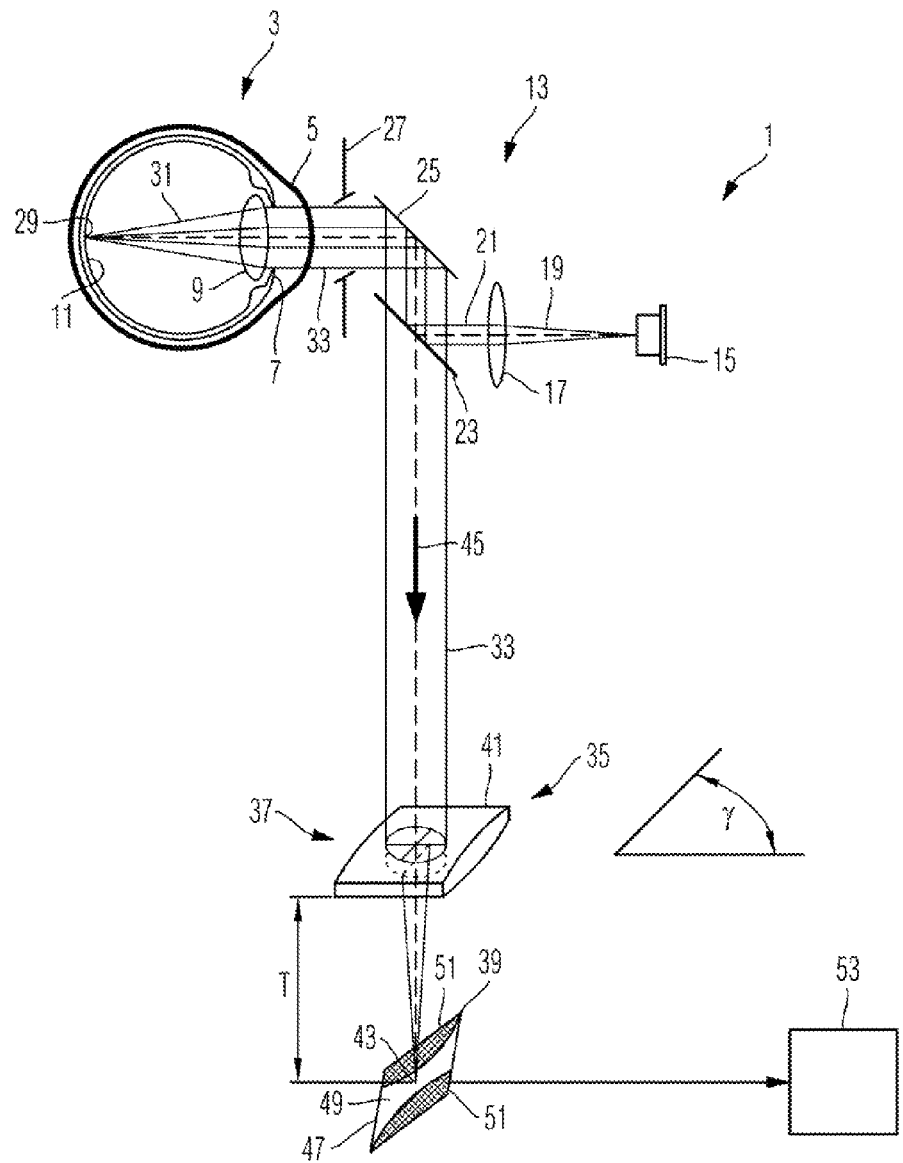
FIG. 1 shows a schematic illustration of an embodiment of an apparatus for determining an ametropia of an eye.

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

FIG. 1 is a schematic illustration of an apparatus 1 for determining an ametropia of an eye 3. The eye 3 comprises a cornea 5, an iris 7, a natural eye lens 9 and a retina 11. The apparatus for determining the ametropia of the eye 3 comprises a beam generation module 13 having a measurement light source 15 such as a laser diode and beam formation optics 17 which may comprise one or multiple lenses. The measurement light source 15 emits light 19 formed as a measurement light beam 21 by the beam formation optics 17. The measurement light beam 21 is first reflected at a semi transparent mirror 23 and then at a tilted mirror 25 so that the measurement light beam 21 is emitted from the apparatus 1 through an optical interface 27 of the apparatus 1 and enters the eye 3. The measurement light beam 21 is formed by the beam formation optics 17 in a way that it illuminates a small spot 29 on the retina 11 of the eye when having traversed the curved cornea 5 and the natural eye lens 9 of the eye 3.

A portion of the light of the measurement light beam 21 incident onto the spot 29 on the retina 11 is reflected or scattered at the retina 11. A portion 31 of this light reflected and scattered, respectively, at the retina 11 traverses the eye lens 9, the iris 7 and the cornea 5 and is emitted as a beam 33 of measurement light from the eye 3 and enters the apparatus 1 through the optical interface 27. If the eye 3 is an emmetropic eye, the beam 33 of measurement light emitted from the eye is a parallel beam.

The beam 33 of measurement light entering the apparatus 1 through the optical interface 27 is reflected at the mirror 25, traverses the semitransparent mirror 23 and passes on to an analysis module 35. The analysis module 35 comprises analysis optics 37 and a detector 39. In the illustrated example, the analysis optics 37 contains a cylinder lens 41. The cylinder lens 41 focuses the beam 33 of measurement light emitted from the emmetropic eye 3 into a line focus 43. That means, according to geometric optics, the focus generated by the cylinder lens 41 is formed along a straight line extending orthogonally to a direction 45 of the analysis beam path.

The detector 39 is a spatially resolving detector having a spread out detection area 47 orientated transversely to the locus line 43 and transversely to the direction 45 of the analysis beam path. This results in a region 49 on the detection 47 illustrated in light shading on the detection surface 47 of FIG. 1 and having a shape of a waist being illuminated by the light of the beam 33, whereas two regions 51 disposed on both sides of the waist-shaped region 49 and illustrated in dark shading are not illuminated by the light of the beam 33.

The apparatus 1 comprises a controller 53 configured to obtain light intensity data detected by the detector 39 and to evaluate the data. By analysis of the shapes of the regions 49 and 51, the controller 53 may determine a distance T by which the line focus 43 is distant from the analysis optics 37.

Figure 2:
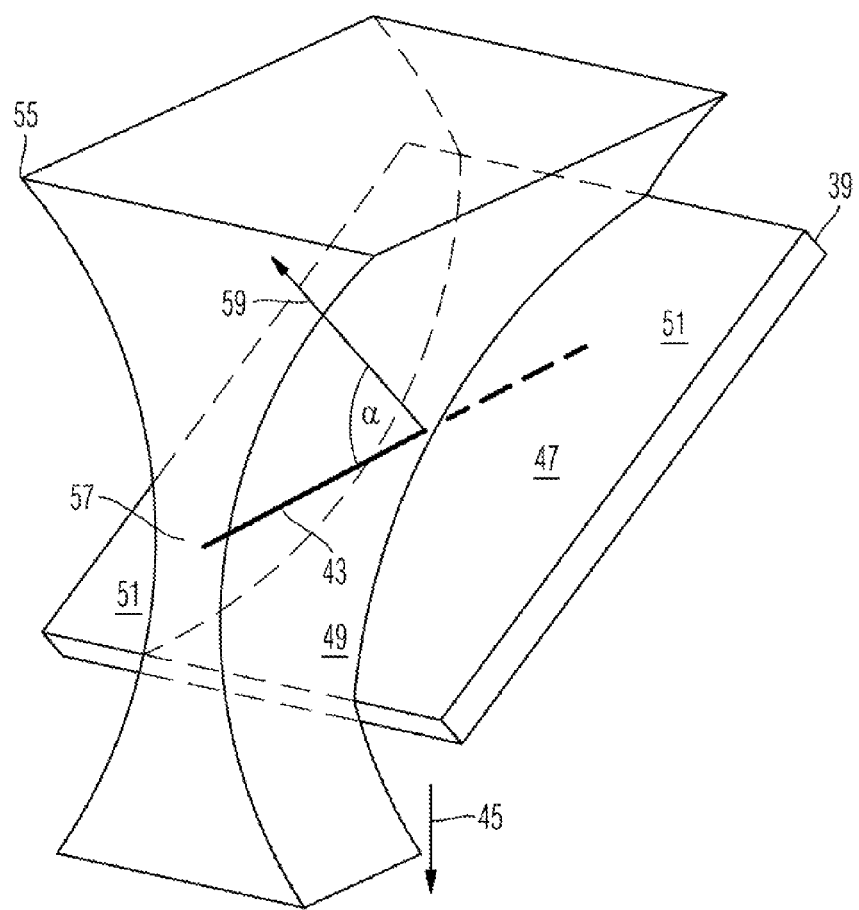
FIG. 2 is a perspective schematic illustration for elucidating a beam waist formed on the detector.

FIG. 2 is a perspective spatial illustration for elucidating the geometric relations in the vicinity of the line focus 43 in the region of the detector 39. In FIG. 2, a waist-shaped body 55 represents a section of the beam 33 of measurement light focused behind the analysis optics 37. The line focus generated according to geometric optics is also referred to by the numeral 43 in FIG. 2. However, the focusing is not achieved exactly in the mathematically thin line 43, but in the shape of a beam waist 57 extending along the line 43. The line 43 of the line focus intersects a surface normal 59, orientated orthogonally to the detection area 47, at an acute angle α of less than 70°. In particular, the angle α may be less than 60° or less than 50°. Furthermore, the angle α may be greater than 10°, greater than 20°, or greater than 30°.

For this configuration, the region 49 of the detection area, onto which the measurement light 55 is also incident, has a shape of a waist, the smallest width of which is found where the line focus 43 intersects the detection area 47. By analyzing the detected light intensities, it is possible to determine the point of intersection between the line focus 43 and the detection area 47 and, based thereon, to determine the distance T of the line focus from the analysis optics 37.

For an emmetropic eye, for which the beam 33 of measurement light being emitted from the eye 3 is a parallel beam, this distance amounts to T(0). If the eye has a spherical refractive error ϕ, the distance T(ϕ) is different from T(0). Hereinafter, the function t(ϕ) characterizes the position of the line focus with respect to the detection area of the detector wherein t(ϕ) denotes the geometric distance of the point of intersection between the line focus 43 generated for the refractive error ϕ and the detection area 47 of the detector 39 from the position on the detection area 47 of the detector 39 where the point of intersection between the line focus 43 and the detection area 47 of the detector 39 is formed when measuring an emmetropic eye having ϕ=0 dpt.

For an eye having a purely spherical refractive error, i.e., no astigmatic refractive error, the position t of the line focus with respect to the detection area in dependence of the spherical refractive error may be given by;

$$t(\varphi) = -\frac{f}{\cos\alpha} \cdot \left( \frac{\frac{1}{\varphi} + d}{f - d - \frac{1}{\varphi}} + 1 \right), \quad (1)$$

wherein the orientation of the coordinate system must be chosen on the detector in a way that Equation (1) is fulfilled with respect to the sign.

In Equation (1).

ϕ is the spherical refractive error, t(ϕ) is the distance of the position, where the line focus 43 intersects the detection area 47 for a spherical, refractive error (p, from the position, where the line focus intersects the detection area 47 for a spherical refractive error ϕ=0 dpt, d is the distance of the pupil of the eye 3 from the cylinder lens 41 along the beam path, f is the focal length of the cylinder lens and α is the angle between the surface normal 59 and the line focus 48 (see FIG. 2).

The focal length f of the cylinder lens 41 and the distance d of the eye 3 from, the cylinder lens 41 should be chosen so that the line focus 43 intersects the detection area of a given geometric configuration if the spherical refractive error to be measured is within a target measurement range. For example, the following values may be used; d=70 mm, f=20 mm for a range of spherical refractive errors of −5 dpt≤ϕ≤+5 dpt. This results in −4 mm≤t(ϕ)≤+4 mm, and, for example, a conventional ⅔-inch detector having an extension of 8.8 mm×8.8 mm may be used.

Figure 3:
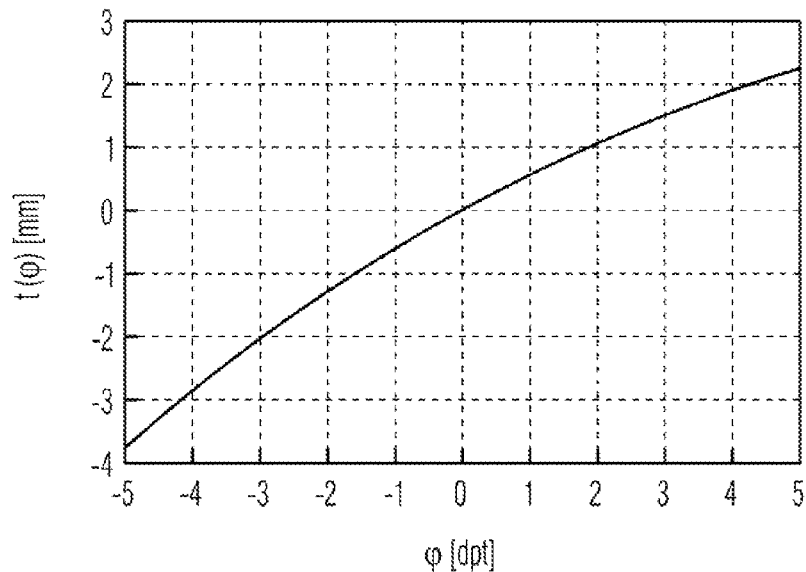
FIG. 3 is a graph showing a relation between a position of a line focus and a spherical refractive error.

The dependency of the position of the line focus along the direction 45 of the analysis beam according to Equation (1) is illustrated in FIG. 3 in dependence of the spherical refractive error ϕ.

Figure 4:
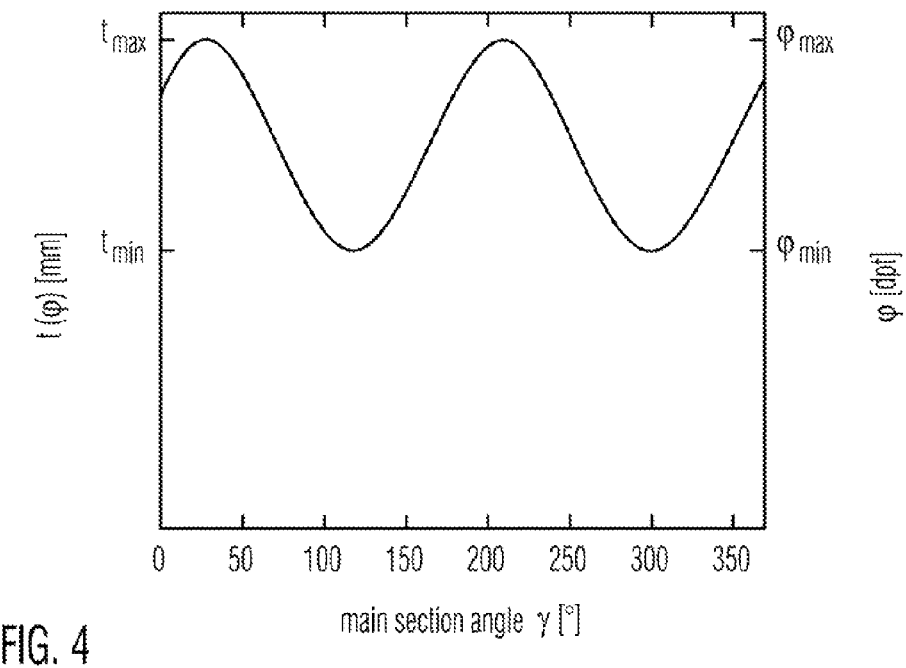
FIG. 4 shows a graph for illustrating a measured position of a line focus in dependence of a main section angle.

For an eye 3 not having an astigmatic refractive error, the position t(ϕ) of the line focus with respect to the detection area is independent of an orientation of the cylinder lens 41 and the detector 39 about the direction 45 of the beam 33 of measurement light. An angle γ representing the orientation of the cylinder lens 41 about the direction 45 may also be referred to as main section angle. By rotating the cylinder lens 41 together with the detector 39 about the axis defined by the direction 45, it is possible to measure the refraction ϕ of the eye in dependence of the main section angle γ. FIG. 4 shows the dependency of the position t(ϕ) of the line focus with respect to the detection area on the main section angle γ. This dependency has an approximately sinusoidal course. The maximum values t(max) thus formed correspond to the spherical refractive error according to a conventional rule, i.e. by inserting the value t(max) into Equation (1), said equation may be solved for die spherical refractive error ϕ. Similarly; the spherical refractive error may be determined by reading the value ϕ at the value t(max) from the graph of FIG. 3.

The amount of the astigmatic refractive error is given by the difference between the minimum value ϕ (min) and the maximum value ϕ (max) in FIG. 4 and may also be determined from Equation (1) or the graph of FIG. 3. The orientation of the astigmatic refractive error can be determined based on the phase of the sinusoidal course of FIG. 4. In the example illustrated in FIG. 4, the minimum is located at a main section angle γ=115° based on which the orientation of the astigmatic refractive error of the eye 3 may be calculated according to the conventional rule used, for example, in the well-known TABO-scheme.

In the example illustrated in FIG. 1, the analysis optics 37 are configured as a cylinder lens 41. However, the analysis optics 37 may also comprise other optical elements different from a cylinder lens 41 and being capable of generating a spread out focus from a parallel light beam, wherein the focus extends along a line. This line does not necessarily need to be a straight line and may also be a line curved in space. Optics capable of generating a line focus are conventionally referred to as anamorphic optics. Accordingly, a cylinder lens is an example of an anamorphic optical element. Also other optical elements and combinations of optical elements capable of generating a line focus may be used in the analysis optics. An example of another such element is a diffractive optical element being designed to have an anamorphic effect and, in particular, the effects of a cylinder lens.

Figure 5:
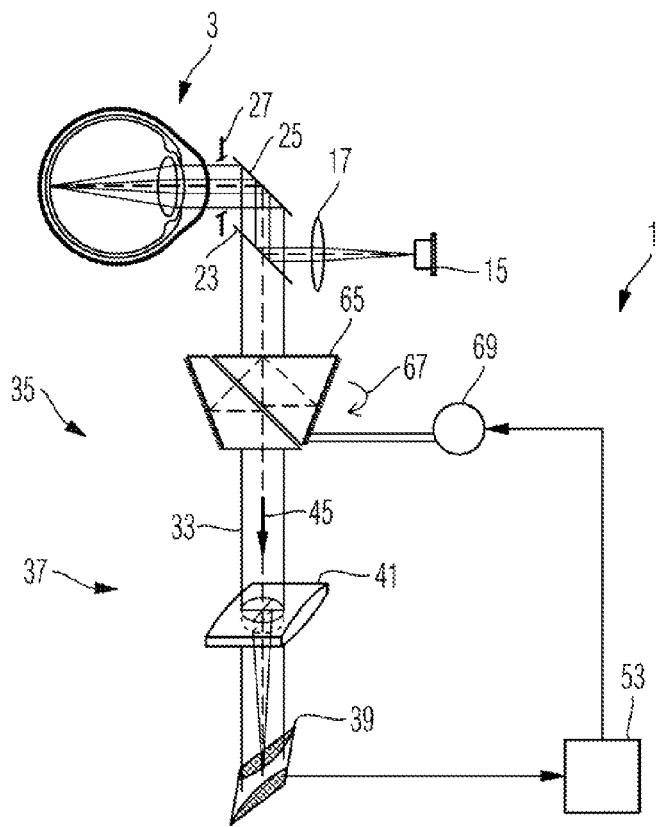
FIG. 5 shows a schematic illustration of an embodiment of an apparatus for determining an ametropia of an eye.

FIG. 5 is a schematic illustration of another embodiment of an apparatus 1 for determining an ametropia of an eye 3. As elucidated with reference to FIGS. 1 and 4, the position of the line focus for an eye having an astigmatic refractive error depends on the main section angle γ, the measurement is conducted for. The main section angle γ may be varied by, as previously described, rotating the analysis module 35 about the beam 33. However, frequent rotating of the detector having electric terminals may lead to failure. For example, due to the rotating, the electric terminals and supply lines to the detector may become deteriorated. In the example of an apparatus 1 for determining the ametropia of the eye 3 illustrated in FIG. 5, the rotating of the detector together with the anamorphic optical element about the axis 45 may be avoided as the analysis optics comprise a prism 65 disposed in the beam path before the anamorphic element 37. The prism 65 is rotatable about the axis of the beam 33 as illustrated by an arrow 67. Hence, the measurement of an astigmatic refractive error may also be performed by rotating merely the prism 65 instead of the entire analysis module, hence, simplifying the mechanical configuration of the analysis module. The rotational position of the prism 65 in the direction of rotation 67 may be set by a motor 69 controlled by the controller 53. The prism 65 is a Schmidt-Pechan-prism.

A rotation of this prism 65 about an angle θ in the direction of rotation 67 results in the beam 33 in the beam path behind the prism being rotated relative to the beam before entering the prism about the angle 2θ.

Figure 8:
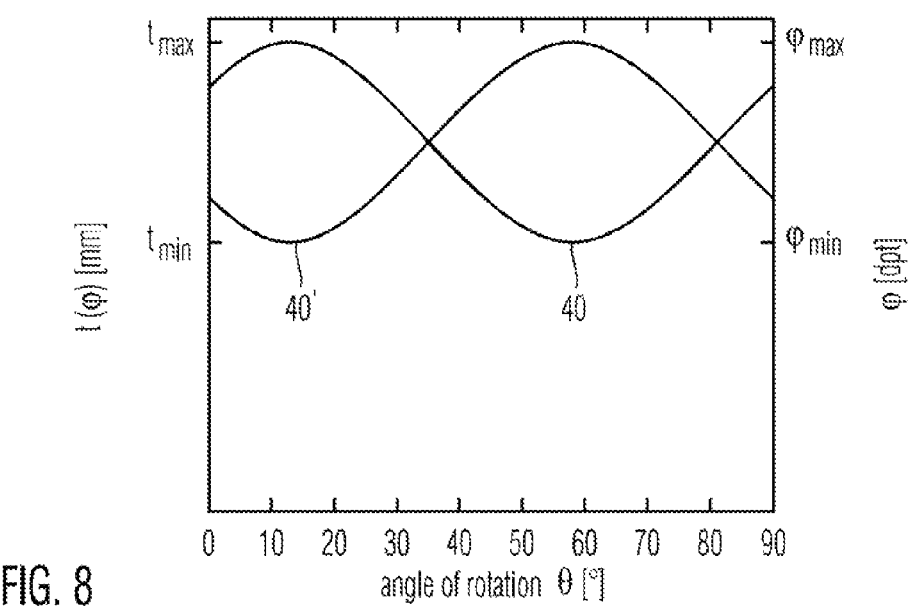
FIG. 8 shows a graph for illustrating a measured position of a line focus in dependence of an angle of rotation.

FIG. 8 shows the dependency of the position t of the line focus on the angle of rotation θ of the prism and the main section angle γ corresponding to this angle of rotation, respectively.

Figure 7:
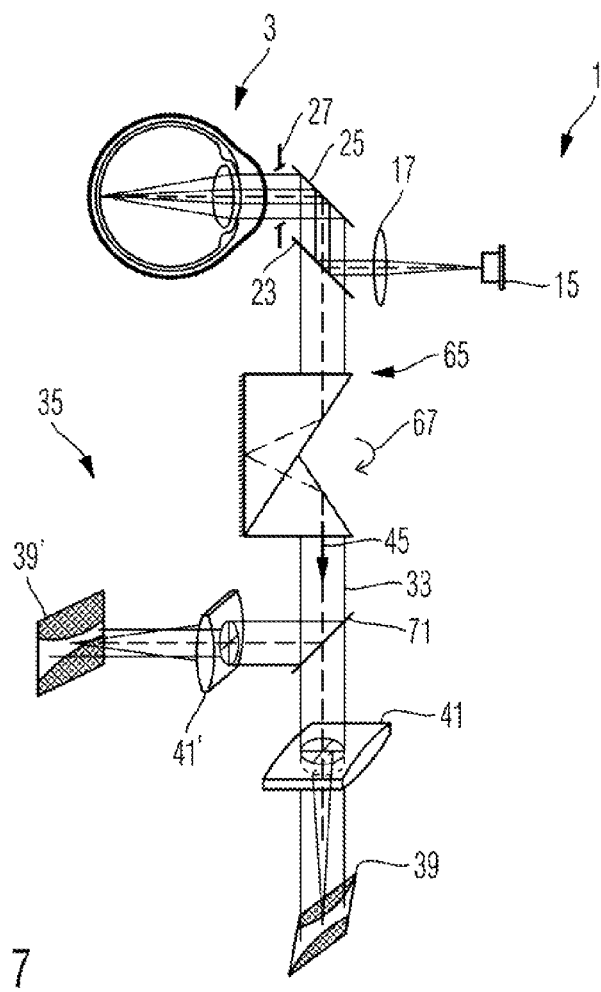
FIG. 7 shows a schematic illustration of an embodiment of an apparatus for determining an ametropia of an eye.

FIG. 7 is a schematic illustration of another embodiment of an apparatus 1 for determining an ametropia of an eye 3. The apparatus illustrated in FIG. 7 has a similar configuration as the apparatus previously elucidated with reference to FIG. 5 in that a prism 65 is used to rotate the beam 33 of measurement light in order to be able to perform measurements at different main section angles γ. In the example illustrated in FIG. 7, the prism 65 is an Abbe-König-prism.

Furthermore, the apparatus 1 illustrated in FIG. 7 differs from the apparatus elucidated with reference to FIG. 5 in that two optics 41 and 41' are provided, each generating a line focus wherein also two detectors 39 and 39' are provided to detect both thus generated line foci. For this, the optics 41 and 41' are configured in a way that they perform, together with the detectors 39 and 39', measurements in main section directions γ and γ' differing from each other by 90°. Both detectors 39 and 39' measure positions of the line focus in dependence of the rotational position of the prism, as illustrated by the curve 40 in the graph of FIG. 8 for the detector 39 and the curve 40' for the detector 39'.

Thereby, it is possible to obtain all desired measurement data when rotating the prism 65 about a smaller total angle of rotation. On the other hand, each of the detectors receives only approximately half of the total available intensity of the beam 33 of measurement light as the available light intensity is split between both optics 41 and 41' and tire detectors 39 and 39' by use of a beam splitter 71.

Figures 9, 10:
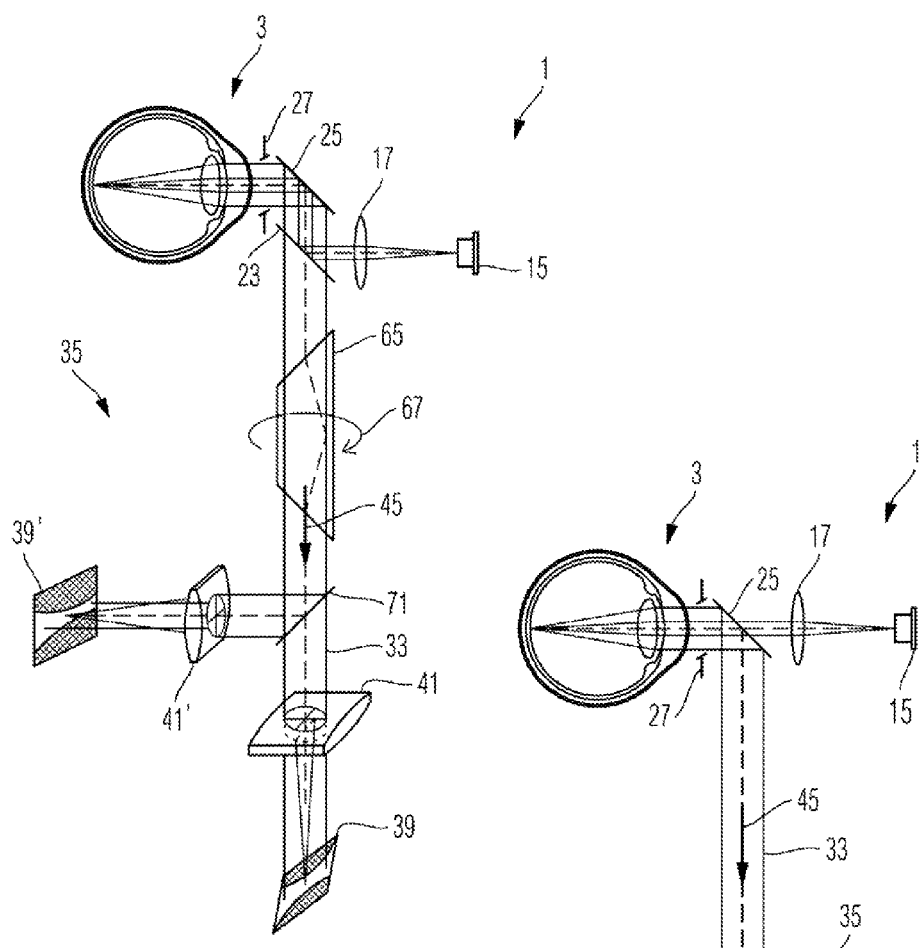
FIG. 9 shows a schematic illustration of an embodiment of an apparatus for determining an ametropia of an eye.
FIG. 10 shows a schematic illustration of an embodiment of an apparatus for determining an ametropia of the eye.

FIG. 9 is a schematic illustration of another embodiment of an apparatus 1 for measuring an ametropia of an eye 3. The configuration of the apparatus 1 according to FIG. 9 is similar to the apparatus previously elucidated with reference to FIG. 7. In contrast thereto, the prism 65 used and being rotatable about the axis of the beam 33 of measurement light in the direction 67 is a Dove-prism.

FIG. 10 is a schematic illustration of another embodiment of an apparatus 1 for determining an ametropia of an eye 3, wherein an analysis module 35 comprises analysis optics 37 and a detector 39. A surface normal of a detection area of the detector 39 is orientated parallel to a direction 45 of the beam 33 of measurement light. However, the analysis optics 37 are configured to generate a line focus intersecting the detection area of the detector 39, whereby the line focus is orientated relative to the direction 45 of the beam 33 at an angle different from 90°. For example, this angle may amount to 45°. For this, in the illustrated example, the analysis optics are configured as a cylinder lens being tilted in the analysis beam path. Furthermore, the analysis optics are rotatable in a direction 67 about the beam 33 in order to be able to perform the measurement for different main section angles.

In this example, the angle of rotation θ of the cylinder lens corresponds to the main section γ, i.e. θ=γ.

Figure 11:
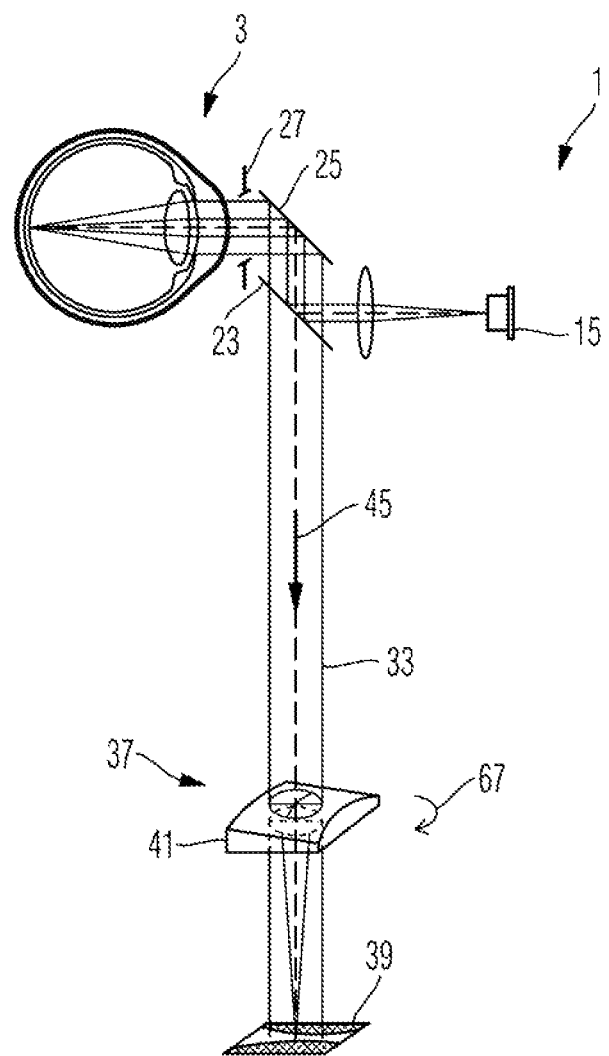
FIG. 11 shows a schematic illustration of an embodiment of an apparatus for determining an ametropia of an eye.

FIG. 11 is a schematic illustration of another embodiment of an apparatus 1 for determining an ametropia of an eye 3. The apparatus of FIG. 11 is similar to the apparatus elucidated with reference to FIG. 10 in that a detection area of a detector 39 is orientated essentially orthogonal to a direction 45 of the beam 33 of measurement light. In contrast to the apparatus elucidated with reference to FIG. 10, the analysis optics 37 are not configured as a cylinder lens but as an anamorphic optical lens element known from FIGS. 5 and 9 of US 2013/0214121 A1. This optical lens element has at least one lens surface having local radii of curvature along a line of the lens surface, wherein the local radii of curvature continuously increase along the line. This results in the distance of the generated line focus from the lens element to be changing along die line focus and, hence, the line focus is orientated at an angle of, for example, less than 70° to the surface normal of the detection area of the detector.

Figure 12A:
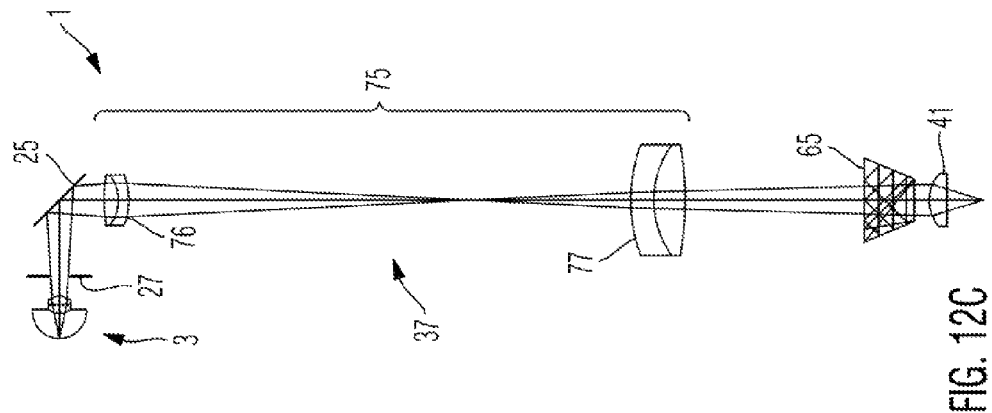
FIGS. 12A to 12C show schematic illustrations of an embodiment of an apparatus for determining an ametropia of an eye and beam paths for different refractive errors of the eye to be measured.
Figure 12B:
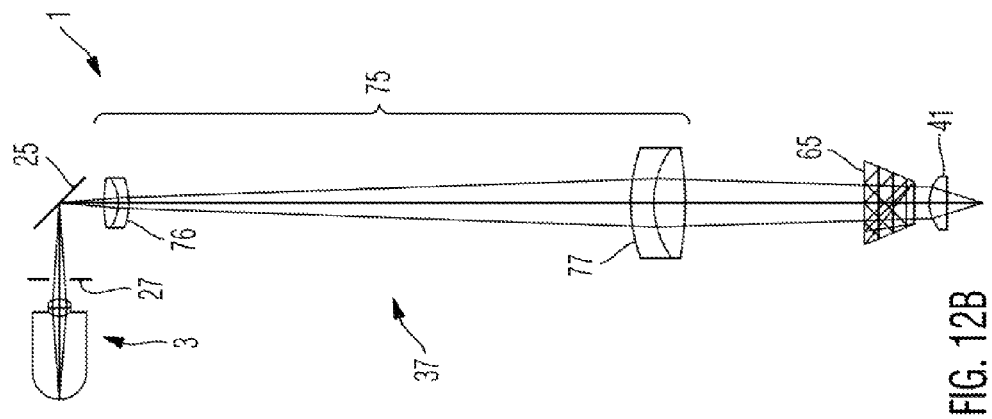
Figure 12C:
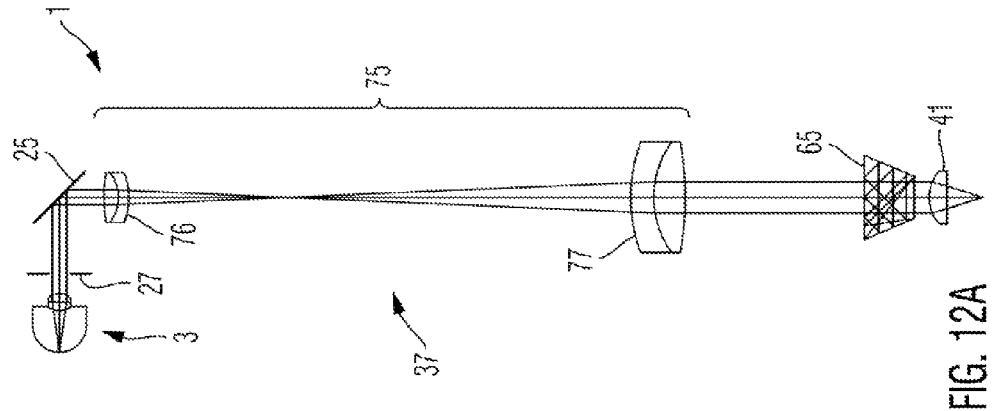

FIGS. 12A, 12B and 12C are schematic illustrations of another embodiment of an apparatus 1 for determining an ametropia of an eye 3. FIG. 12A shows the beam path through the analysis optics of the apparatus for a measurement of an emmetropic eye, FIG. 12B shows the beam path through the analysis optics of the apparatus for the measurement of a myopic eye having −25 dpt, and FIG. 12C shows the beam path through the analysis optics of the apparatus for a measurement of a hyperopic eye having +22 dpt.

The apparatus 1 according to FIGS. 12A, 12B and 12C is similar to the apparatus elucidated with reference to FIG. 5 in that a rotatable Schmidt-Pechan-prism 65 is used to perform the measurement in multiple main section directions. In addition, the analysis optics 37 of the apparatus 1 of FIGS. 12A, 12B and 12C comprise a telescope 75 disposed in the beam path between, the optical interface 27 and the detector 39. The telescope 75 is a magnifying telescope. In the elucidated embodiment, the telescope 75 is a Kepler-telescope having two lenses 76 and 77 disposed at a distance from each other, each themselves being configured as cemented elements. If the telescope 75 has a lateral image magnification m, the longitudinal imaging scale amounts to $m^2$. This results in the change of the position t(φ) of the point of intersection of the line focus with the detection area is magnified in dependence of the spherical refractive power φ by the telescope by a factor $m^2$. The position t(φ) of the point of intersection of the line focus with the detection area may thus be written according to Equation (1) considering the magnification m of the telescope 75 by:

$$t(\varphi) = -\frac{f}{\cos\alpha} \cdot \left( \frac{\frac{m^2}{\varphi} + d'}{f - d' - \frac{m^2}{\varphi}} + 1 \right), \quad (2)$$

wherein, in equation (2), d' denotes the distance of the image of the pupil of the eye 3, the image being generated by the telescope, from the anamorphic optical element 41.

By using the magnifying telescope 75 in the analysis beam path, it is possible, for a given size of the detector, to increase the measurement range for the measurement of the spherical refractive power, in the illustrated example, the lens 76 has a focal length f1=70 mm, the lens 77 has a refractive length f2=154 mm, resulting in a measurement range increased by the factor $m^2=(154/70)^2=4.84$.

For further illustration of the measurement method used herein, FIGS. 13A, 13B, 13C and 13D illustrate light intensities measured by the detector for different values of the refractive error, as detected by an array of pixels of a two-dimensional detector, wherein the array of pixels is orientated in the detection area in a way that the points of intersection between die line focus and the detection area for different refractive errors are disposed on this array of pixels. Similar intensities may also be measured using an accordingly orientated one-dimensional line detector.

Figure 13A:
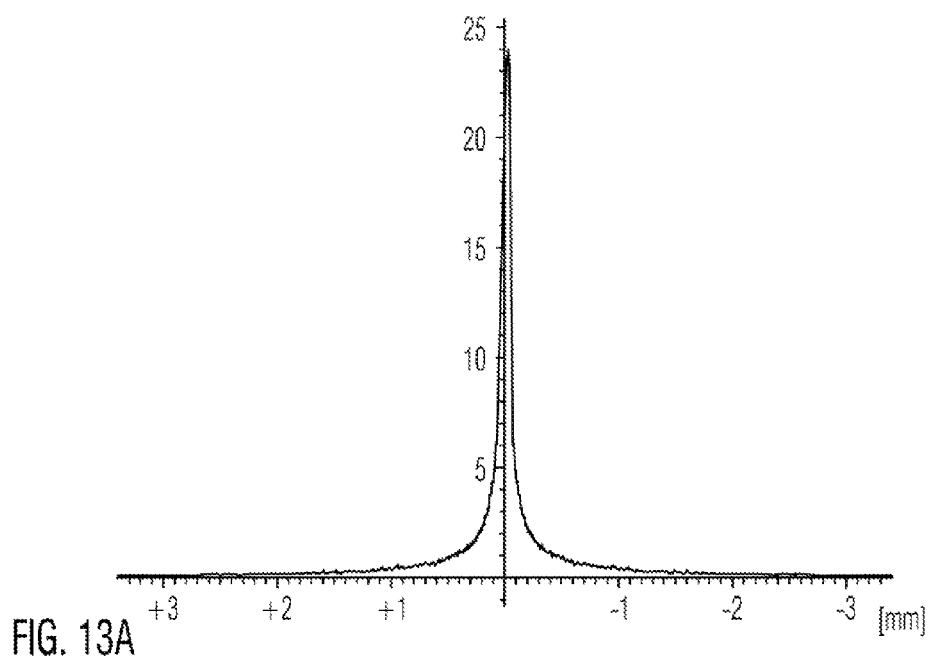
FIGS. 13A to 13D show light intensities measured for different refractive errors for the eye to be measured and being measured using the system shown in FIGS. 12A, 12B, 12C.

FIG. 13A shows the measurement for an emmetropic eye. The coordinate system of the array of pixels is chosen so that the intensity maximum of the emmetropic eye is at approximately x=0 mm so that t (0 dpt)=0 mm is fulfilled.

Figure 13B:
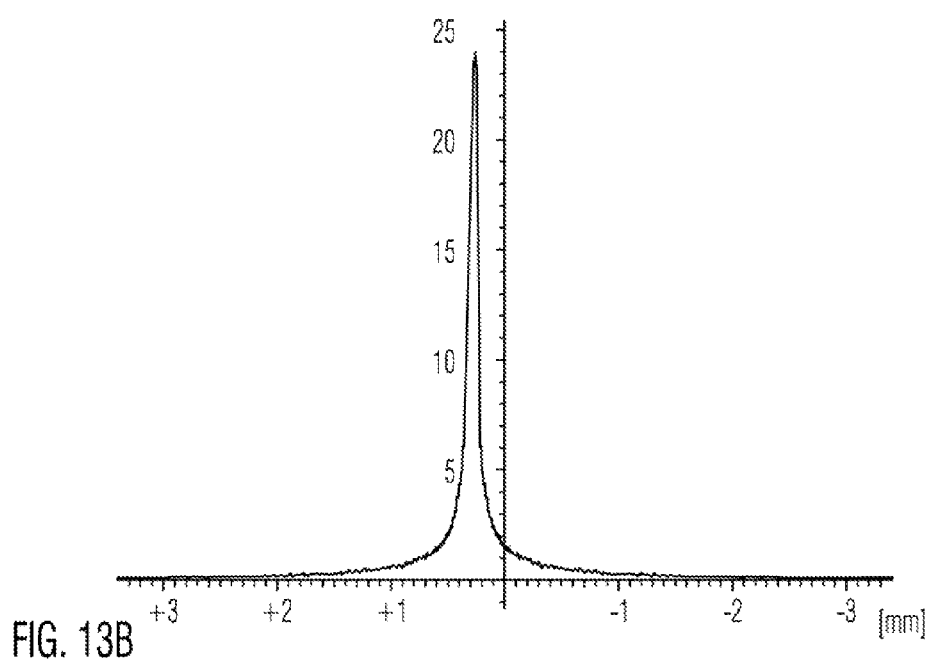

FIG. 13B shows the measurement for a hyperopic eye having +2.5 dpt. The intensity maximum is at approximately x=+0.3 mm. By solving equation (2) $t(\phi)=+0.3$ mm for $\phi$, $\phi$ is about +2.5 dpt.

Figure 13C:
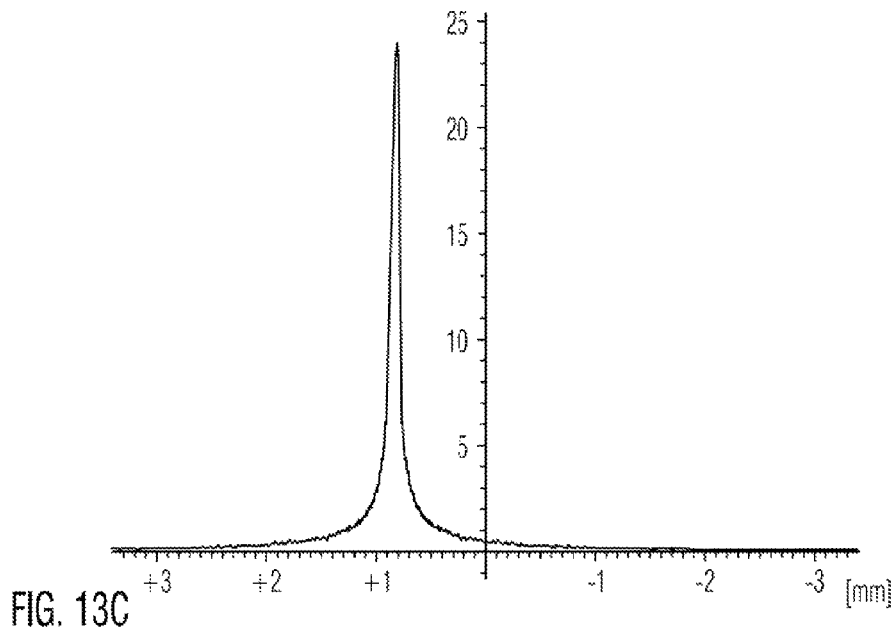

FIG. 13C shows the measurement for a hyperopia eye having +7.5 dpt. The intensity maximum is at approximately x=+0.9 mm. By solving Equation (2) to $t(\phi)=+0.9$ mm for $\phi$, $\phi$ is about +7.5 dpt.

Figure 13D:
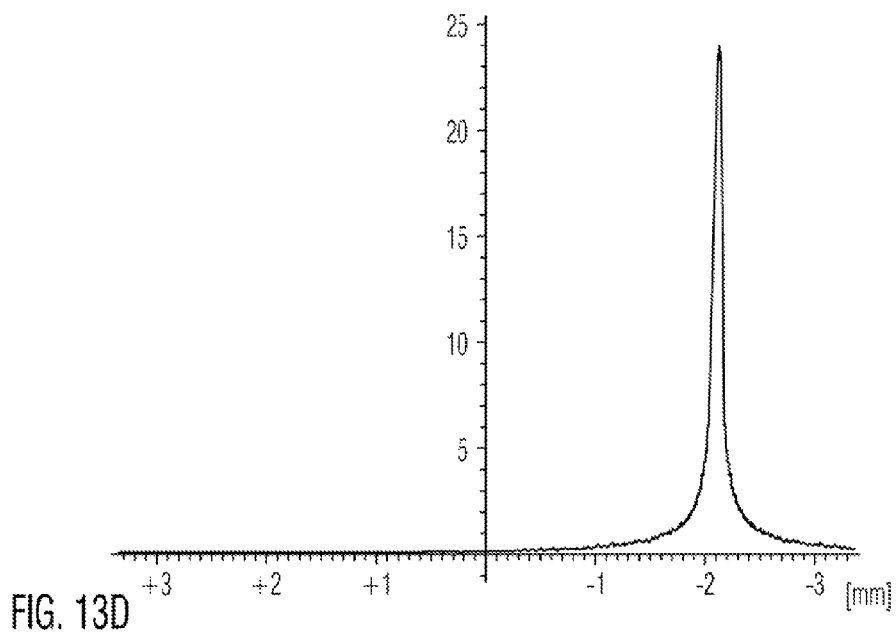

FIG. 13D shows the measurement for a myopic eye having −20 dpt. The intensity maximum is at approximately x=−2.18 mm. By solving Equation (2) to $t(\phi)=-2.18$ mm for $\phi$, $\phi$ is about −20 dpt.

Figure 14:
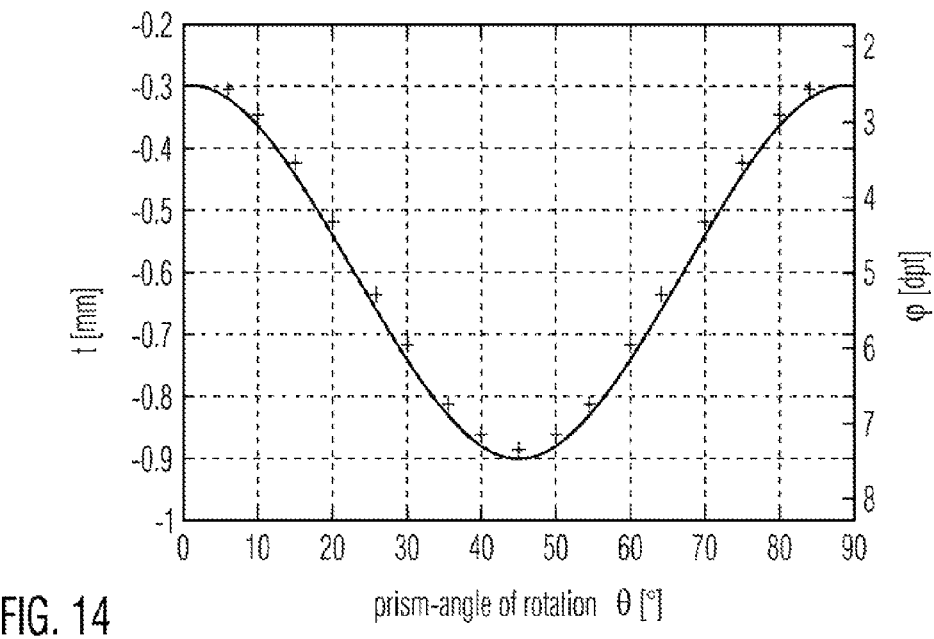
FIG. 14 shows positions of a line focus in dependence of a prism-angle of rotation obtained by simulation using a model eye.

FIG. 14 shows a graph associated with the embodiment elucidated with reference to FIG. 12, wherein the position of the line focus is plotted in dependence of the angle of rotation θ of the prism 65. The points marked by crosses are obtained by simulation performed on the basis of a model eye. In practice, such data may also be obtained by measuring a real eye. In the illustrated example, the model eye does not have farther imaging errors of higher order beside a spherical refractive error of 7.5 dpt and an astigmatic refractive error of −5 dpt. The model eye has the minimum refraction of 2.5 dpt in the main section of the plane of projection so that the position of the axis of the astigmatic refractive error amounts to 0° for the chosen rotation. According to Equation (2), using α=−45°, f=20 mm and d=0 mm, the following values are obtained:

$$t(2.5 dpt) = -\frac{20 \text{ mm}}{\cos(45°)} \cdot \left( \frac{\frac{4.84}{2.5 dpt}}{20 \text{ mm} - \frac{4.84}{2.5 dpt}} + 1 \right) = 0.295 \text{ mm,}$$

and $$t(7.5 dpt) = -\frac{20 \text{ mm}}{\cos(45°)} \cdot \left( \frac{\frac{4.84}{7.5 dpt}}{20 \text{ mm} - \frac{4.84}{7.5 dpt}} + 1 \right) = 0.905 \text{ mm.}$$

The curve shown as a solid line in FIG. 14 is obtained while assuming a sinusoidal course between both extreme positions of the line focus. Apparently, the analytically determined curve approximates the measurement points determined by simulation relatively well.

Figure 15:
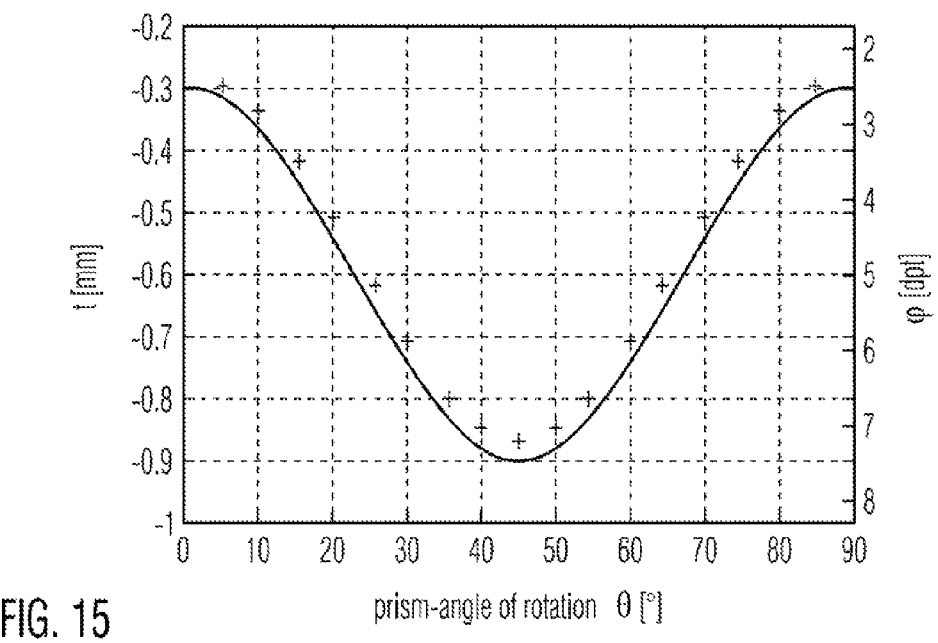
FIG. 15 shows positions of a line focus in dependence of a prism-angle of rotation obtained by simulation using another model eye.

FIG. 15 shows a graph of an examination on the basis on a model eye, similar to the examination elucidated with reference to FIG. 14. The model eye underlying the examination of FIG. 15 again has a spherical refractive error of 7.5 dpt, an astigmatic refractive error of −5 dpt for a position of the axis of 0° relative to the plane of projection. In contrast to the model eye underlying the examination of FIG. 14, the model underlying the examination of FIG. 15 has a spherical aberration of higher order. The points illustrated by crosses are obtained by simulation using a ray tracing method. However, in practice, such data may also be obtained by measuring a real eye. Deviations from the sinusoidal course illustrated by the solid line are apparent. In particular, this leads to a decrease of the measured amount of the astigmatic refractive error if the astigmatic refractive error is calculated based on the difference between the measured minimum values and maximum values. Therefore, it may be advisable to determine spherical aberrations of higher order by evaluating the measured data or not to use Equation (2), but a more complex equation or function values previously calculated and available as a table. Furthermore, a limiting aperture reducing the beam cross section may be used, for example, in the region of the optical interface so that aberrations of higher order become negligible.

Figure 16:
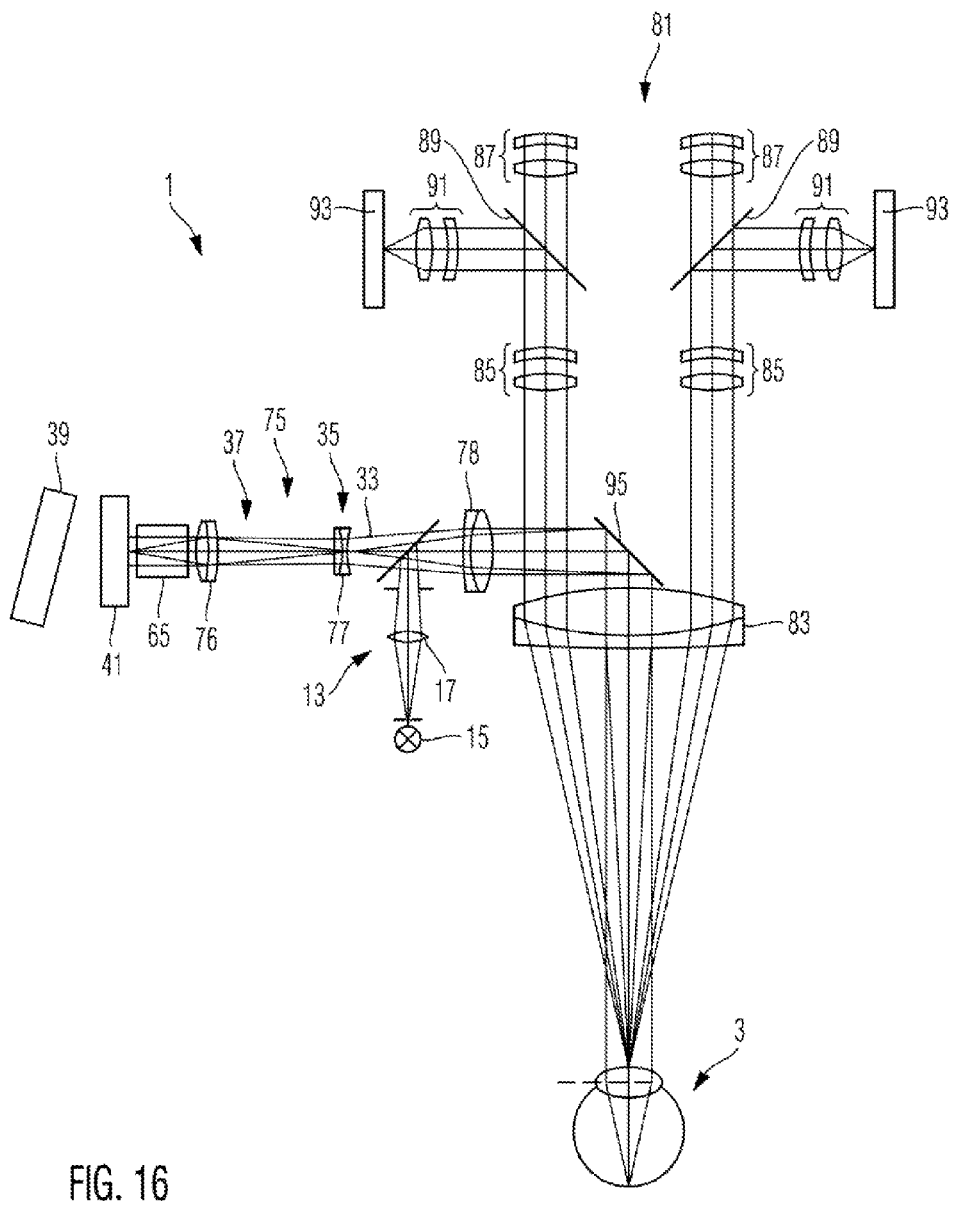
FIG. 16 shows a schematic illustration of an embodiment of an apparatus for determining an ametropia of an eye.

FIG. 16 is a schematic illustration of another embodiment of an apparatus 1 for determining an ametropia of an eye 3. The apparatus 1 comprises a beam generation module 13 having beam formation optics 17 and a measurement light source 15 as well as an analysis module 35 having a detector 39 and analysis optics 37. The analysis optics 37 comprise magnifying optics 75 having lenses 76, 77 and 78, a prism 65, rotatable about an axis of the beam 33 of measurement light, and an anamorphic optical element 41 configured to generate a line focus intersecting a detection area of the detector 39.

The apparatus for determining the ametropia of the eye 3 is integrated with a surgery microscope 81 which may be used to generate a magnified illustration of the eye 3. In particular, the microscope 81 enables a surgeon to perform a surgery on the eye 3 while observing the eye 3 using the microscope 81. Due to the integration with the apparatus for determining the ametropia of the eye, it is possible to determine the ametropia of the eye during the surgery in a simple way. In order to be able to also measure aphakic eyes, i.e. eyes, the natural lens of which are removed, during the surgery, the measurement range for the spherical refractive error amounts to −15 dpt to +30 dpt for this embodiment.

The microscope 81 is a stereo microscope having a pair of observation beam paths, wherein each of both the observation beam paths traverses a common objective lens 83, a separate zoom system 85 and a separate ocular 87 wherein the surgeon may look into both the oculars 87 using his eyes in order to perceive a magnified image of a portion of the eye 3. Furthermore, in both the beam paths, beam splitters 89 may be disposed to direct a portion of the light available for the imaging onto a camera detector 93 via camera optics 91 so that the magnified image of the eye 3 may also be recorded electronically. In the example shown in FIG. 15, the tilted mirror 95 is disposed behind the objective lens 83, seen in direction of the imaging beam path of the microscope. However, the tilted mirror may be disposed before the objective lens, i.e. underneath the objective lens in the illustration of FIG. 15.

Background information regarding the integration of ametropia measurement entities with surgery microscopes may be obtained from DE 10 2008 047 400 A1 and DE 10 2010 024 806 A1 showing the integration of wave front sensors with surgery microscopes.

The analysis light beam for determining the ametropia of the eye also traverses the objective lens 83 and is deflected at a mirror 95 and directed to the analysis optics 37. The beam cross section directly above the objective lens 83 may be regarded as the previously elucidated optical interface of the apparatus for determining the ametropia of the eye.

Figure 17:
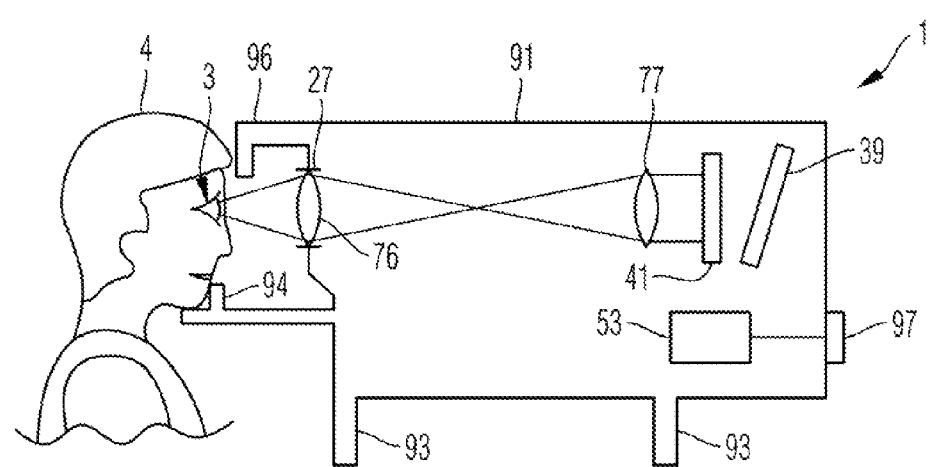
FIG. 17 shows another schematic illustration of an embodiment of an apparatus for determining an ametropia of an eye.

FIG. 17 is a schematic illustration of another embodiment of an apparatus 1 for determining an ametropia of an eye 3. This apparatus is configured as an independent device which may be employed, for example, in an office of an eye specialist or an optometrist. The apparatus 1 has a configuration of the beam formation optics and the analysis optics previously elucidated with reference to FIGS. 1 to 14. The apparatus 1 comprises a closed housing 91 having an opening defining the optical interface for the beam formation optics and the analysis optics and may also comprise a lens 76 of a telescope of the analysis optics. The housing 91 comprises a stand support 93 and body part rest elements 94 and 96. If a patient presses his head with the chin against the rest element 94 and his forehead against the body part rest element 96, his eye 3 is disposed opposite to the optical interface 27 in a way that the ametropia of the eye 3 may be determined using the apparatus and the apparatus may output ametropia-data via an interface 97. The interface may comprise, for example, an electric terminal for a computer network or a monitor with which the ametropia-data may be visually illustrated.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

The invention claimed is:

1. An apparatus for determining an ametropia of an eye, the apparatus comprising:
- a beam generation module comprising a measurement light source and beam formation optics;
- an analysis module comprising a detector and analysis optics; and
- a controller;
- wherein the beam formation optics are configured to form a measurement light beam from light emitted by the measurement light source so that the measurement light beam is emitted from the apparatus at an optical interface;
- wherein the analysis optics are disposed in an analysis beam path between the optical interface and the detector;
- wherein the analysis optics are configured to focus a parallel light beam, entering through the optical interface, along a predetermined line extending transverse to a direction of the analysis beam path;
- wherein the detector is a spatially resolving detector having a detection area;
- wherein an acute angle between a surface normal of the detection area and the predetermined line is less than 80°; and
- wherein the controller is configured to obtain light intensity data detected by the detector and to determine ametropia-data representing the ametropia of the eye based on the light intensity data.

2. The apparatus according to claim 1, wherein the ametropia-data represent at least one of a spherical refractive error of the eye, and an amount and orientation of an astigmatic refractive error of the eye.

3. The apparatus according to claim 1, wherein the predetermined line intersects the detection area.

4. The apparatus according to claim 1, wherein the analysis optics comprise at least one anamorphic optical element.

5. The apparatus according to claim 1, wherein the analysis optics comprise one of a cylinder lens and at least one optical element having effects of a cylinder lens.

6. The apparatus according to claim 1, wherein the analysis optics comprise at least one diffractive optical element.

7. The apparatus according to claim 1, wherein the analysis optics comprise at least one optical lens element having at least one lens surface having, along a line on the lens surface, local radii of curvature continuously increasing along the line.

8. The apparatus according to claim 1, wherein the analysis optics comprise an optical element traversed by the analysis beam path and rotatable relative to the detector about an axis of rotation orientated parallel to the direction of the analysis beam path.

9. The apparatus according to claim 8, wherein the rotatable optical element comprises one of an anamorphic optical element, an optical element having effects of a cylinder lens, a cylinder lens, a diffractive optical element and an optical lens element having at least one lens surface having, along a line on the lens surface, local radii of curvature continuously increasing along the line.

10. The apparatus according to claim 8, wherein the rotatable optical element comprises a prism.

11. The apparatus according to claim 10, wherein the prism is one of a Schmidt-Pechan-prism, an Abbe-König-prism and a Dove-prism.

12. The apparatus according to claim 8, wherein the analysis optics comprise a drive controlled by the controller and configured to rotate the rotatable optical element about the axis of rotation.

13. The apparatus according to claim 12, wherein the controller is configured to rotate the rotatable optical element to a plurality of rotational positions about the axis of rotation, to obtain light intensity data for each of the plurality of rotational positions, and to determine the ametropia-data based on the plurality of obtained light intensity data.

14. The apparatus according to claim 13, wherein the controller is configured to determine a value representing a position of a beam waist of a light beam incident onto the detector based on each of the plurality of obtained light intensity data.

15. The apparatus according to claim 14, wherein the controller is configured to determine an amount of a spherical refractive error of the eye based on an extremum value of the values representing the positions of the beam waist.

16. The apparatus according to claim 14, wherein the controller is configured to determine an astigmatic refractive error of the eye based on a difference between a minimum value and a maximum value of the values representing the positions of the beam waist.

17. The apparatus according to claim 14, wherein the controller is configured to determine an orientation of an astigmatic refractive error of the eye based on a phase of a dependency of the values, representing the positions of the beam waist, on the rotational position.

18. The apparatus according to claim 1, further comprising a beam splitter which is disposed in a beam path between the beam generation module and the optical interface and in a beam path between the optical interface and the analysis module.

19. The apparatus according to claim 1, wherein the analysis optics comprise a magnified-imaging telescope disposed in a beam path between the optical interface and the detector.

20. The apparatus according to claim 1, further comprising at least one rest element positioned relative to the optical interface so that an eye of a user is positioned opposite to the optical interface if a predetermined portion of a head of the user is pressed against the rest element.

21. The apparatus according to claim 1, further comprising a housing encasing the beam generation module and analysis module, wherein the housing has an opening, in particular, defining the optical interface.

22. The apparatus according to claim 1, further comprising a microscope having an imaging beam path traversing the optical interface.

23. The apparatus according to claim 22, wherein the microscope is a stereo microscope.

* * * * *

UNITED STATES PATENT AND TRADEMARK OFFICE
CERTIFICATE OF CORRECTION

PATENT NO. : 9,259,152 B2
APPLICATION NO. : 14/577235
DATED : February 16, 2016
INVENTOR(S) : Seesselberg et al.

Page 1 of 3

It is certified that error appears in the above-identified patent and that said Letters Patent is hereby corrected as shown below:

In the Specification

In Column 1, Line 9, delete "which," and insert -- which --, therefor.

In Column 1, Line 14, delete "present," and insert -- present --, therefor.

In Column 1, Line 28, delete "such," and insert -- such --, therefor.

In Column 1, Line 31, delete "light," and insert -- light --, therefor.

In Column 1, Line 32, delete "light," and insert -- light --, therefor.

In Column 2, Line 23, delete "beam," and insert -- beam --, therefor.

In Column 2, Line 24, delete "light," and insert -- light --, therefor.

In Column 2, Line 46, delete "80°" and insert -- 60° --, therefor.

In Column 2, Line 60, delete "position," and insert -- position --, therefor.

In Column 3, Line 10, delete "position," and insert -- position --, therefor.

In Column 3, Line 35, delete "referred," and insert -- referred --, therefor.

In Column 3, Lines 50-51, delete "optical," and insert -- optical --, therefor.

In Column 4, Line 13, delete "wherein," and insert -- wherein --, therefor.

In Column 4, Line 47, delete "formed," and insert -- formed --, therefor.

In Column 4, Line 49, delete "that," and insert -- that --, therefor.

In Column 5, Line 22, delete "light," and insert -- light --, therefor.

Signed and Sealed this
Fourteenth Day of June, 2016

Michelle K. Lee
*Director of the United States Patent and Trademark Office*

In Column 5, Line 32, delete "apparent," and insert -- apparent --, therefor.

In Column 6, Lines 31-32, delete "semi transparent" and insert -- semitransparent --, therefor.

In Column 6, Line 61, delete "locus" and insert -- focus --, therefor.

In Column 7, Line 31, delete "ϕ, the distance T(ϕ)" and insert -- φ, the distance T(φ) --, therefor.

In Column 7, Line 32, delete "t(ϕ)" and insert -- t(φ) --, therefor.

In Column 7, Line 33, delete "t(ϕ)" and insert -- t(φ) --, therefor.

In Column 7, Line 34, delete "Intersection" and insert -- intersection --, therefor.

In Column 7, Line 35, delete "ϕ" and insert -- φ --, therefor.

In Column 7, Line 40, delete "ϕ=0" and insert -- φ=0 --, therefor.

In Column 7, Line 56, delete "Equation (1)." and insert -- Equation (1), --, therefor.

In Column 7, Line 57, delete "ϕ" and insert -- φ --, therefor.

In Column 7, Line 58, delete "t(ϕ)" and insert -- t(φ) --, therefor.

In Column 7, Line 59, delete "spherical," and insert -- spherical --, therefor.

In Column 7, Line 60, delete "(p," and insert -- φ, --, therefor.

In Column 7, Line 61, delete "ϕ=0" and insert -- φ=0 --, therefor.

In Column 7, Line 67, delete "focus 48" and insert -- focus 43 --, therefor.

In Column 8, Line 2, delete "from," and insert -- from --, therefor.

In Column 8, Line 7, delete "dpt≤ϕ≤+5" and insert -- dpt≤φ≤+5 --, therefor.

In Column 8, Line 8, delete "mm≤t(ϕ)≤+4" and insert -- mm≤t(φ)≤+4 --, therefor.

In Column 8, Line 9, delete "mm×8.8" and insert -- mm×6.6 --, therefor. (Second Occurrence)

In Column 8, Line 14, delete "ϕ." and insert -- φ. --, therefor.

In Column 8, Line 16, delete "t(ϕ)" and insert -- t(φ) --, therefor.

In Column 8, Line 23, delete "ϕ" and insert -- φ --, therefor.

In Column 8, Line 25, delete "t(ϕ)" and insert -- t(φ) --, therefor.

In Column 8, Line 31, delete "die spherical refractive error ϕ. Similarly;" and insert -- the spherical refractive error φ. Similarly, -- therefor.

CERTIFICATE OF CORRECTION (continued)
U.S. Pat. No. 9,259,152 B2

In Column 8, Line 33, delete "ϕ" and insert -- φ --, therefor.

In Column 8, Line 35, delete "ϕ (min)" and insert -- φ (min) --, therefor.

In Column 8, Line 36, delete "ϕ (max)" and insert -- φ (max) --, therefor.

Figure 6:
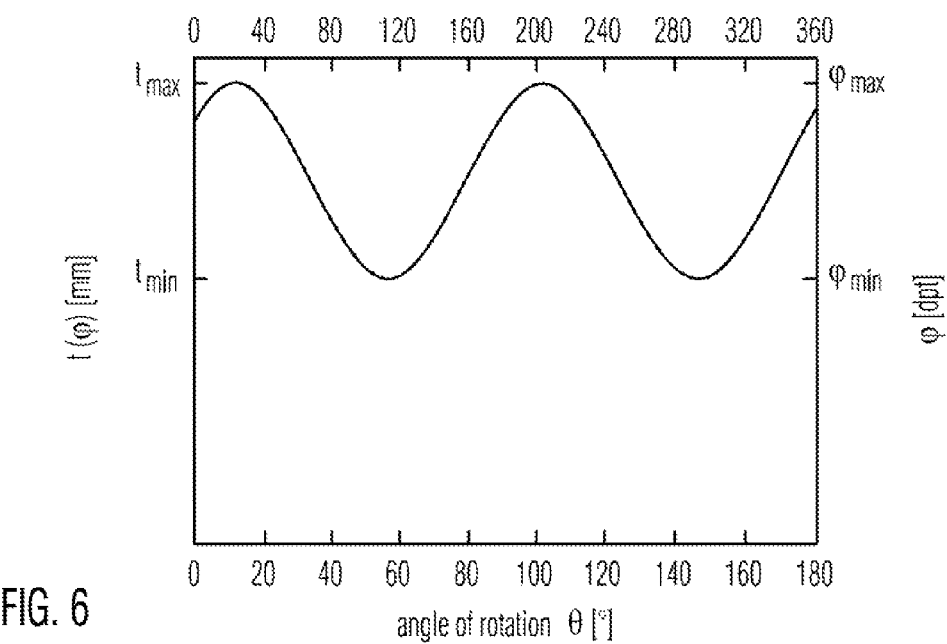
FIG. 6 shows a graph for illustrating a measured position of a line focus in dependence of a main section angle and an angle of rotation, respectively.

In Column 9, Line 21, delete "FIG. 8" and insert -- FIG. 6 --, therefor.

In Column 9, Line 50, delete "tire" and insert -- the --, therefor.

In Column 10, Line 23, delete "die" and insert -- the --, therefor.

In Column 10, Line 41, delete "between," and insert -- between --, therefor.

In Column 10, Line 48, delete "t(ϕ)" and insert -- t(φ) --, therefor.

In Column 10, Line 50, delete "ϕ" and insert -- φ --, therefor.

In Column 10, Line 51, delete "t(ϕ)" and insert -- t(φ) --, therefor.

In Column 11, Line 2, delete "power, in" and insert -- power. In --, therefor.

In Column 11, Line 12, delete "die" and insert -- the --, therefor.

In Column 11, Line 23, delete "t(ϕ)=+0.3 mm for ϕ, ϕ is" and insert -- t(φ)=+0.3 mm for φ, φ is --, therefor.

In Column 11, Line 25, delete "hyperopia" and insert -- hyperopic --, therefor.

In Column 11, Line 27, delete "t(ϕ)=+0.9 mm for ϕ," and insert -- t(φ)=+0.9 mm for φ, --, therefor.

In Column 11, Line 28, delete "ϕ" and insert -- φ --, therefor.

In Column 11, Line 31, delete "t(ϕ)=-2.18 mm for ϕ, ϕ is" and insert -- t(φ)=-2.18 mm for φ, φ is --, therefor.

In Column 11, Line 40, delete "farther" and insert -- further --, therefor.

In Column 12, Line 64, delete "2010 024 806 A1" and insert -- 2010 024 606 A1 --, therefor.